(12) United States Patent
Bragg et al.

(10) Patent No.: US 6,796,697 B1
(45) Date of Patent: Sep. 28, 2004

(54) ILLUMINATION DELIVERY SYSTEM

(75) Inventors: Chris Bragg, Oakland, CA (US);
Daniel Scott, San Jose, CA (US);
Eliezer Rosengaus, Palo Alto, CA (US)

(73) Assignee: KLA-Tencor, Inc., San Jose, CA (US)

( * ) Notice: Subject to any disclaimer, the term of this patent is extended or adjusted under 35 U.S.C. 154(b) by 0 days.

(21) Appl. No.: 10/140,486

(22) Filed: May 7, 2002

Related U.S. Application Data

(60) Provisional application No. 60/327,059, filed on Oct. 4, 2001.

(51) Int. Cl.[7] .............................. F21V 7/04; G02B 6/00
(52) U.S. Cl. ...................... 362/554; 362/330; 362/331; 362/268; 362/558
(58) Field of Search ................................ 362/554, 551, 362/326, 330, 331, 268, 558; 385/115, 116, 119, 120, 121, 901

(56) References Cited

U.S. PATENT DOCUMENTS

| | | | | |
|---|---|---|---|---|
| 2,825,260 A | * | 3/1958 | O'Brien ...................... 385/116 |
| 4,964,692 A | * | 10/1990 | Prescott .................... 350/96.24 |
| 5,255,336 A | * | 10/1993 | Kuder et al. .................. 385/46 |
| 5,268,749 A | * | 12/1993 | Weber et al. ............... 356/446 |
| 5,638,479 A | * | 6/1997 | Takami et al. .............. 385/124 |
| 5,754,278 A | * | 5/1998 | Kurtz ........................... 355/67 |
| 5,917,588 A | * | 6/1999 | Addiego ..................... 356/237 |
| 6,447,133 B1 | * | 9/2002 | Eschke et al. ................ 362/31 |
| 6,509,982 B2 | * | 1/2003 | Steiner ........................ 359/15 |
| 2003/0081428 A1 | * | 5/2003 | Neta .......................... 362/558 |

* cited by examiner

Primary Examiner—Stephen Husar
Assistant Examiner—Sharon Payne
(74) Attorney, Agent, or Firm—Deborah W. Wenocur

(57) ABSTRACT

An illumination delivery system provides a spatially and angularly uniform shaped beam output with sufficient intensity to illuminate a sample surface for defect inspection. Light is transmitted through a shaped fiber optic bundle, a homogenizer, a diffuser, and an optional focusing optics system.

59 Claims, 7 Drawing Sheets

ILLUMINATION DELIVERY SYSTEM

This application claims the benefit of provisional application No. 60/327,059 filed Oct. 4, 2001.

FIELD OF THE INVENTION

This invention deals with illumination delivery systems, in particular for application in a macroscopic defect inspection system for patterned wafers.

BACKGROUND OF THE INVENTION

Macroscopic defect inspection systems employed in semiconductor processing have the capability of discerning defect anomalies from a patterned background. Generally, repetitive structures are compared, using dark field scattered profiles or bright field images, between a minimum of three die to locate defects. Detectable defect sizes using this type of system range from the order of tens of microns to whole-wafer sized defects, up to 200 or 300 mm. Spatial and angular uniformity of the illumination over the full field of view are crucial to achieving reproducibly accurate results, and to avoid changes in the diffraction pattern from the wafer.

Tool architectures can be comprised of a zero-dimensional light source (a point source), a one-dimensional light source (a line source), or a two-dimensional light source (area source). In the first case, the point source and the substrate move relative to each other in both x and y directions, or radially and angularly. In the second case, the line source and the substrate typically move relatively in one direction. In the case of a full wafer area source, the substrate and source do not move relative to each other. If the area source is less than the area of the wafer, then movement of the source and substrate are as in the point source case.

The Viper inspection tool from KLA-Tencor is a macroscopic defect inspection system which employs a one-dimensional (i.e. line) light source, which is scanned across the wafer surface in one direction only, perpendicular to the line of the light source. The Viper-2401 system, which is designed for inspection of 200 mm diameter wafers, is described in U.S. Pat. No. 5,917,588 by Addiego, which is hereby incorporated by reference in its entirety.

In the Viper tool architecture, the substrate of interest is scanned by a line illumination source and the resulting dark field scatter profile or bright field image is collected by a linear array camera. The Viper 2401 system utilizes a cylindrically shaped lamp such as a fluorescent tube, illustrated in FIG. 1 in dark-field configuration. Lamp tube 2 functions as a line illuminator. Outgoing light rays 4 emerge from line aperture 6 to shine on wafer surface 8. Scattered rays 10 are focused by imaging lens optics 12 onto linear sensor array 13.

Improvements in the light source, including greater spatial and angular uniformity, and increasing intensity, are important factors in the development of improved defect detection systems, particularly as wafer size increases, for example up to 300 mm diameter. Tube lamps may not provide uniform illumination profiles (including intensity as a function of wavelength, and direction) at the substrate plane over the length of interest, nor may they be able to sustain the same constant profile as a function of length over time. A lamp that can maintain a constant illumination profile over time may be usable with suitable spatial corrections applied; however, a lamp whose illumination profile changes with age is more difficult to use successfully since spatial corrections would need to be adjusted as well.

An inherent problem with extended light sources such as fluorescent lamps is the difficulty in using a closed loop control system to stabilize the illumination profile as a function of time, since sensing the light output at any point on the lamp does not necessarily reflect the light output changes elsewhere.

Another problem with the use of fluorescent lamps in defect detection tools, particularly as the diameter of the wafers and therefore the necessary length of the illumination source, increases, is the desirability of increased intensity, for several reasons. First, if pixel size were maintained fixed as wafer size increased, and therefore the number of pixels across the wafer increased, a large increase in complexity of data analysis and slower throughput would result. It is therefore desirable to increase the pixel size in proportion to wafer size increase, and thereby maintain the total number of pixels fixed. By doing so, the spatial sampling frequency is lowered which can cause problems. If the sampling frequency is lowered below the Nyquist value, particularly at feature edges where the spatial feature frequency is highest, aliasing effects may occur. In order to avoid this, the numerical aperture of the collection lenses must be lowered so as to reduce the high frequency component of the signal. The lower numerical aperture requires higher intensity light. Secondly, higher intensity light will also increase the signal to noise ratio, yielding a more precise and accurate image within each pixel. Thirdly, increased intensity is necessary to enable polarization or color imaging, both of which involve filtering out a large portion of the light. The intensity of fluorescent lamps is insufficient for these purposes. Additionally, there is a large amount of light intensity wasted from a fluorescent bulb source due to lack of angular control.

The use of a high intensity point light source would solve the problem of insufficient intensity, and would additionally make feasible a closed-loop control approach to insure stability over time. However, in order to be utilized in a line-scan application such as the Viper tool, the light from a point source would be required to be reshaped into a uniform line.

SUMMARY OF THE INVENTION

It is therefore an object of this invention to provide an illumination delivery system including a long linear light source having intense, spatially and temporally uniform output across its length.

It is a further object of this invention to provide an illumination delivery system including a long linear light source which is adaptable to closed loop control.

It is a further object of this invention to provide an illumination delivery system including a long linear light source which has precise control of incident angle and of incident angular spread.

These objects are met by directing the output of a point light source into a shaped fiber optic bundle, then afterwards mixing, diffusing, and focusing the fiber optic output to provide an intense, uniform linear light source with well defined incident angle.

DETAILED DESCRIPTION OF THE INVENTION

Figure 1:
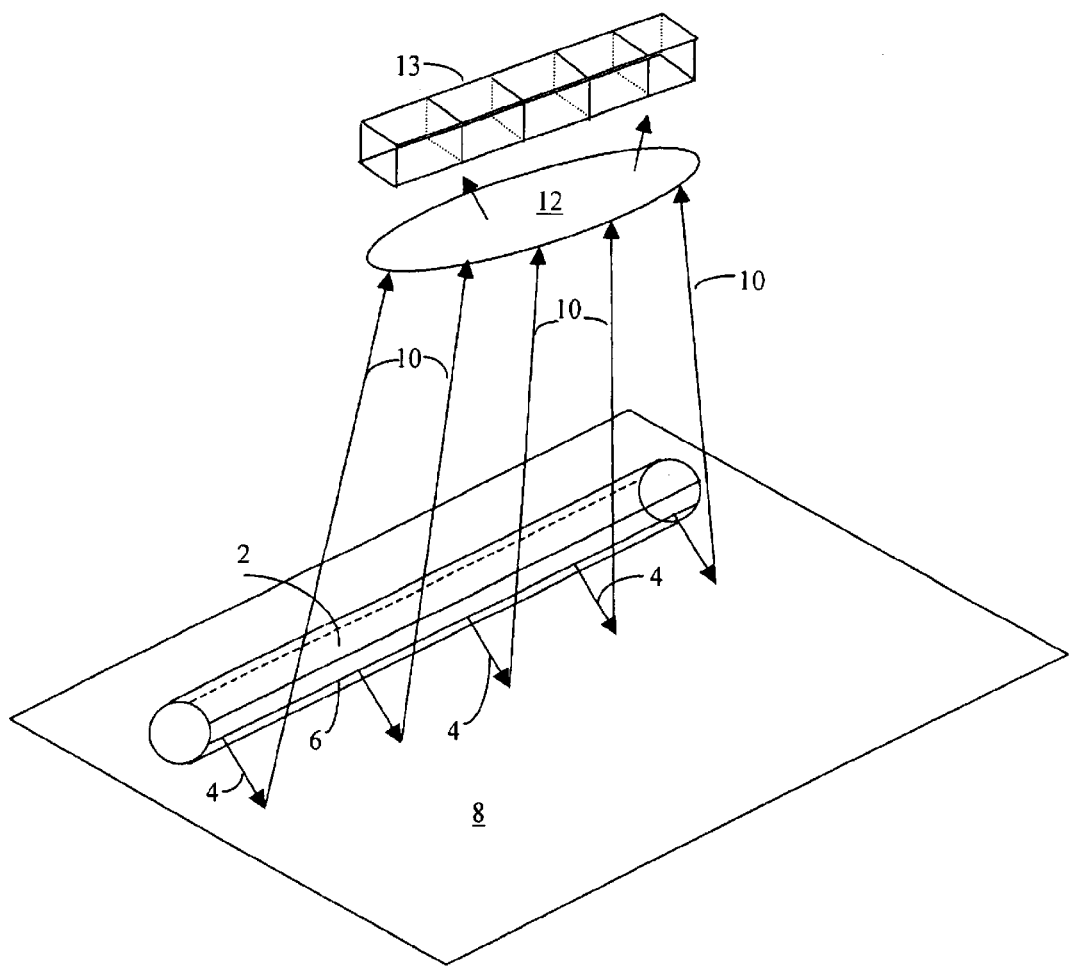
FIG. 1 illustrates a prior art extended light source for a macro defect inspection system.
Figure 2:
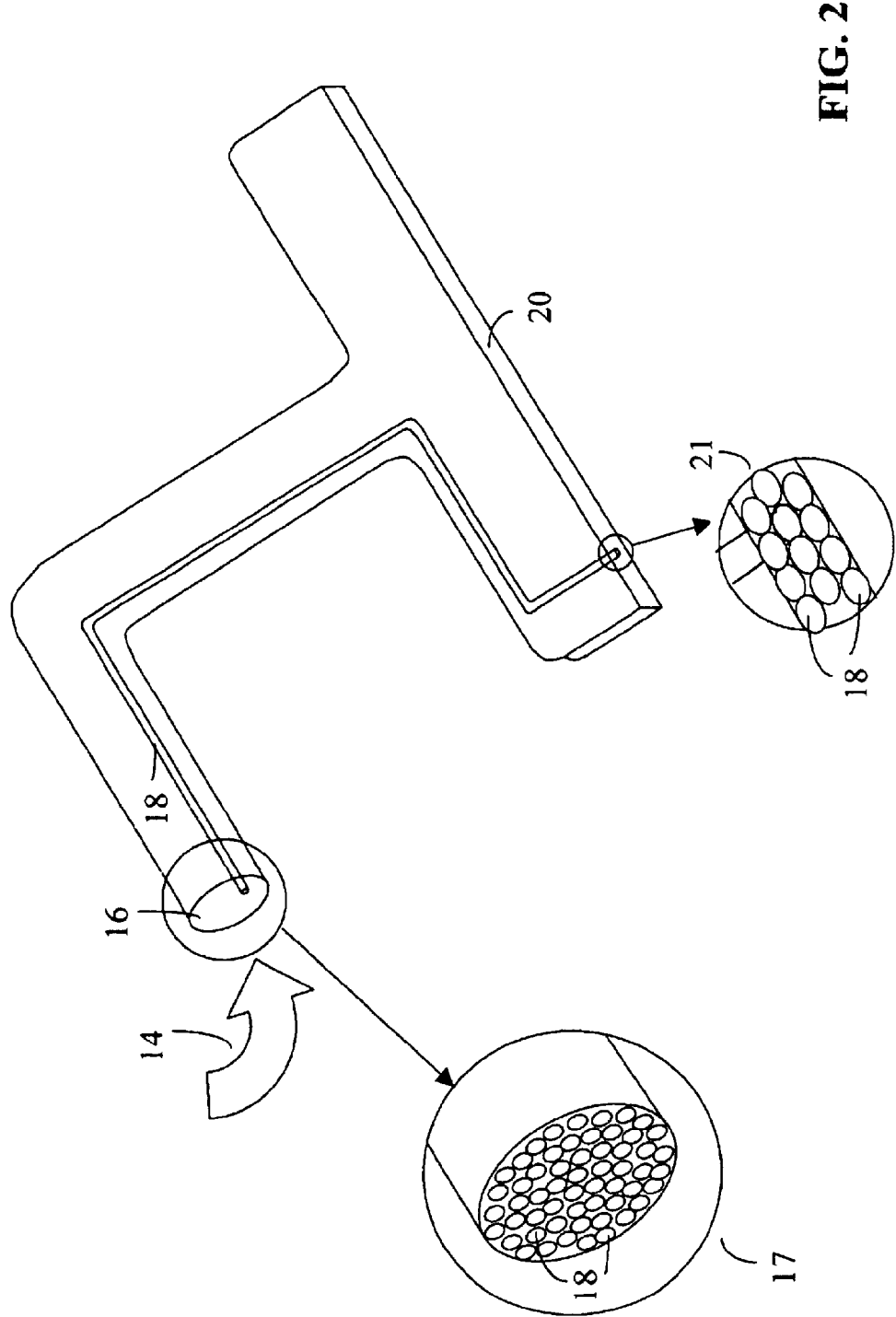
FIG. 2 illustrates a fiber optic configuration yielding a linear fan-shaped light source.

The use of shaped fiber optic bundles is known in the art. A description of shaped fiber optic bundles and their manufacture is found in U.S. Pat. No. 5,887,102, which is hereby incorporated by reference. An approach to creating line illumination is to direct the output of a light source, which may be a point light source by way of example, into a fiber optic bundle, and then shaping the bundle to produce the desired shaped output illumination. For example, a round lamp's output could be directed into a circular cross section of optical fibers that are then tailored into a fan-like shape to produce a line of light. In order to avoid transmitting the image of the source to the output of the fiber output, the fibers are randomly distributed in the bundle to provide the best mixing within the resulting shaped source. FIG. 2 illustrates such a fiber optic configuration. Illumination input 14, e.g. from a round lamp, is directed into circular cross section 16 of optical fibers 18. Enlargement 17 of cross section 16 shows fibers 18. The fibers are tailored into a fan-like shape to produce fiber optic line source 20. Enlargement 21 of a section of line source 20 is shown. Advantages of a fiber optic delivery system include:

1. The use of fiber optics removes constraints on the source geometry, and allows the use of a wider variety of source types, such as broadband vs. narrowband, or varying power level.

2. Use of fiber optics allows the source to be located remotely from the substrate to be illuminated while maintaining good transmission efficiency.

3. Fiber optic bundles enable variation in illumination output shape (for example, an increase in the length of a line source) with minimal variation in overall output uniformity and no dramatic change in illumination density, given the same fiber type and total cross sectional area.

One difficulty encountered by the use of fiber optics for illumination delivery in macro inspection systems is that the individual fibers can be on the same order of size as the resolution of the imaging system. For example, typical fiber diameters are about 50 microns, and the pixel size of the detection system, particularly when scanning 300 mm wafers, may be 40 microns. The impact of this is that the size of imperfections in the fiber bundle at its output may be of the same order as that of the defects being detected if the fiber output is close to the illumination surface, or if imaging optics image the fiber onto the surface.

Figure 3A:
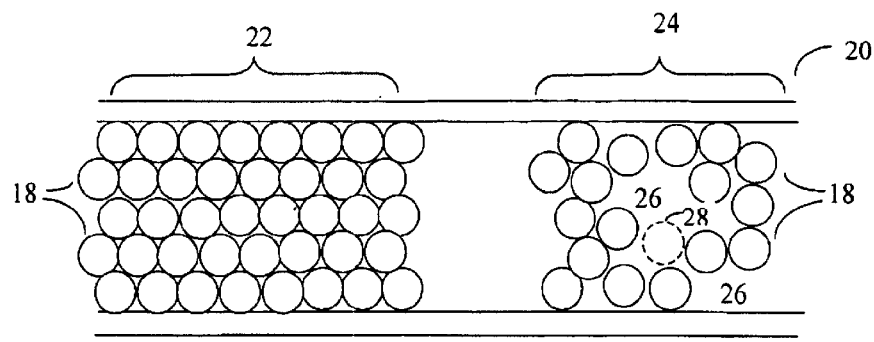
FIG. 3a illustrates gap- or void-type imperfections in a fiber optic output.

FIG. 3a illustrates a first type of imperfection in the fiber bundle output, i.e., voids which may result from uneven shaping or from broken fibers, caused by such factors as face polishing, scratching, or chipping of the fibers. The end view of the fiber output of line source 20 is shown. Region 22 illustrates ideal, uniform, and tight packing of fibers 18. Region 24 shows typical as-built packing, including gaps 26 and broken fibers 28. Although the inaccuracies due to such voids are mitigated by the finite numerical aperture of the individual fibers and the mixing that occurs as light propagates from the fiber line to the surface of the object under test, the non-uniformities may still be visible. A gap in the directed light provided by the fibers may reveal itself as an unilluminated streak in the image in a line scan system.

Figure 3B:
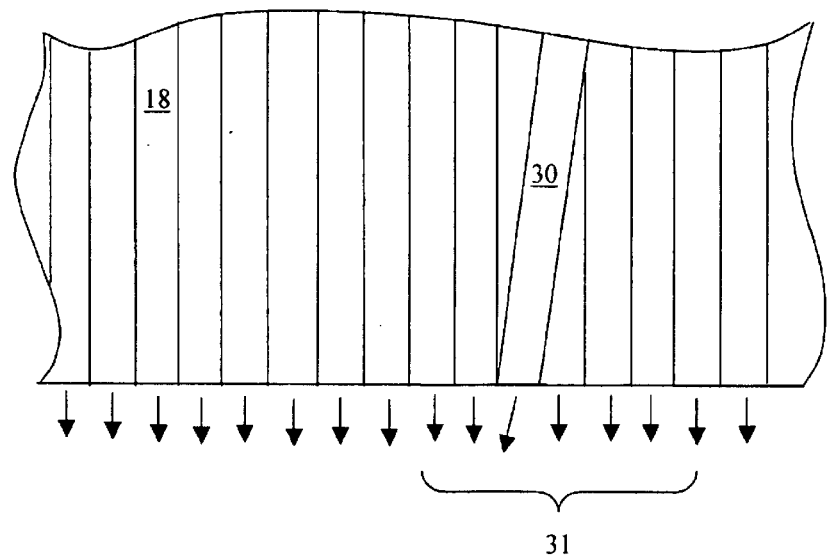
FIG. 3b illustrates non-parallel fiber type imperfections in a fiber optic output.

FIG. 3b illustrates a second type of imperfection in the fiber bundle output, i.e., non-parallel fibers. A side view of the fiber output is shown. In the fabrication of a fiber optic bundle, ideally the fibers 18 are drawn out and held parallel, and thus, ideally, the output of a fiber bundle should be light emerging in a uniform direction. In practice, however, some of the fibers 30 may be bent or otherwise not be parallel with the bulk, and thus give rise to an angular variation in the resulting illumination output 31 which may be unacceptable.

Our invention addresses the aforementioned difficulties encountered in the use of fiber optics for illumination delivery in macro inspection systems. The inventive approach is to combine the features of certain optical components on the output of the fiber bundle. The inventive approach can be applied to any geometric arrangement of fibers, though a fiber bundle shaped to produce a line source will be utilized in the description of the embodiments.

Figure 4:
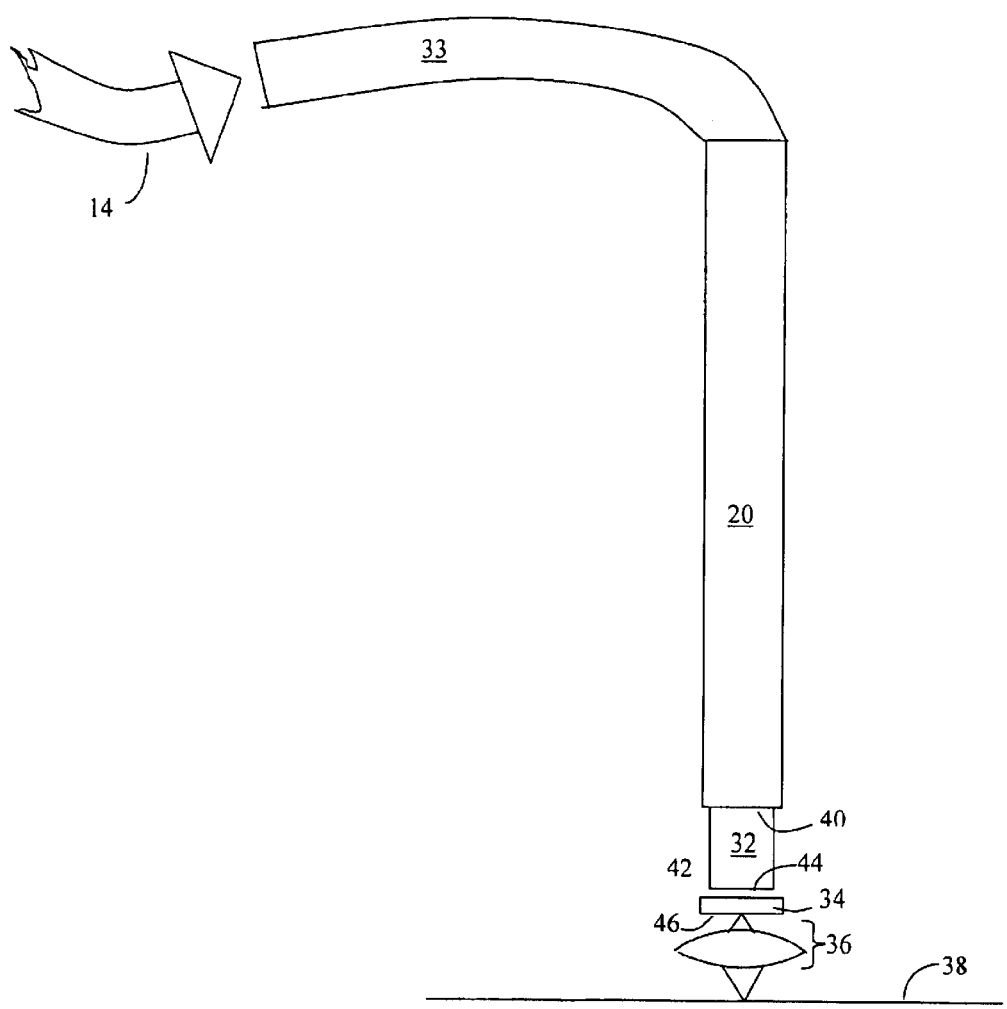
FIG. 4 illustrates a side view of an embodiment of the inventive structure, including fiber bundle, waveguide or "mixing slab", diffusing medium, and lens system.

FIG. 4 shows a side view of an embodiment of our invention. Light output 14 from a lamp is carried by a fiber bundle 33 which is formed into a linear fan-shaped array 20. The fiber output light passes directly into a homogenizer 32 which may be a single waveguide, an array of fibers, or a "mixing slab" having good optical transmission, then through a diffusing medium 34 and finally through an optional lens system 36, which is comprised of one or more lenses, onto the sample 38. Input end 40 of mixing slab 32 is placed at a distance in the range between 0 and 3 mm from the end of fiber fan 20; input end 42 diffuser 34 is between 0 and 3 mm from output end 44 of mixing slab 32; lens system 36 is between 5 and 25 mm from output end 46 of diffuser 34.

Figure 5:
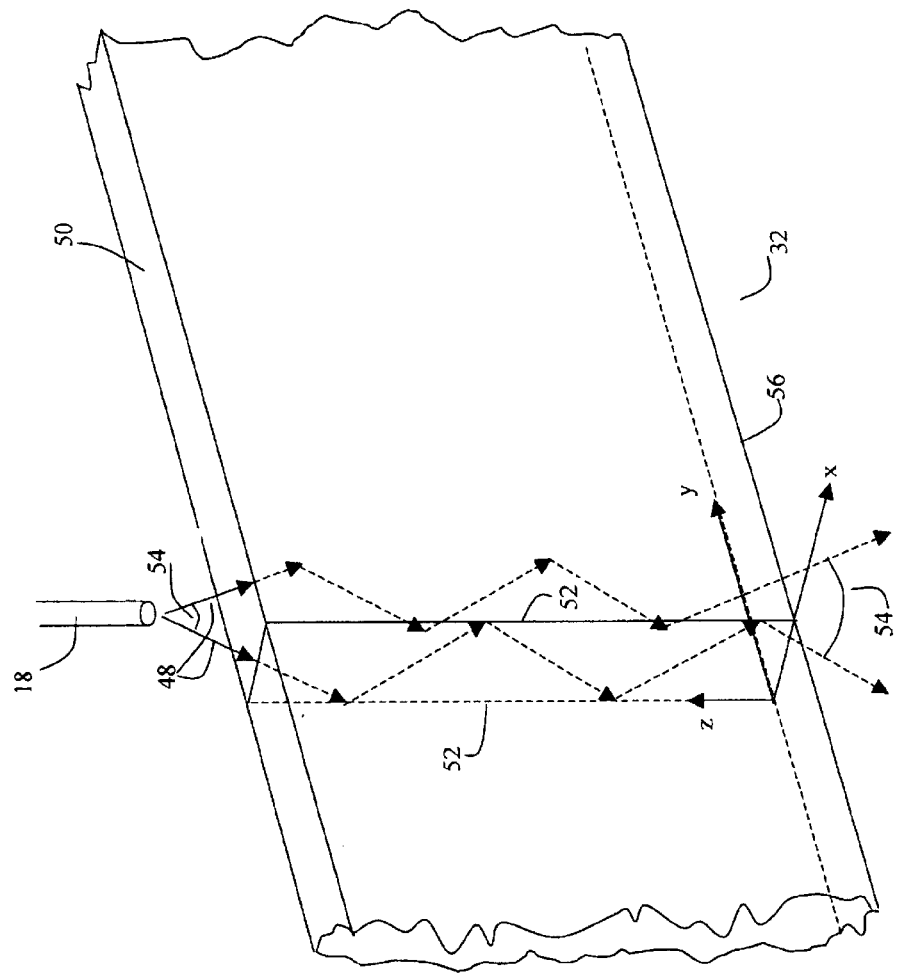
FIG. 5 illustrates the operation of the mixing slab.

The operation of the mixing slab 32 is illustrated in FIG. 5. A mixing slab is a one-dimensional analog to a homogenizing rod, wherein light rays 48 entering at one end 50 undergo total internal reflection at all sidewalls 52 encountered. The mixing slab functions in the same way, except that one dimension, labeled "y" in FIG. 5, is so large that it is ignorable because essentially no reflections will occur in that dimension. Homogenizing occurs in only one dimension, labeled "x" in FIG. 5. Outgoing light from individual fibers 18 has an angular spread 54 having a well-defined value, i.e., a well-defined numerical aperture (NA). The multiple reflections occurring as the beams from the fibers pass through the mixing slab serve the function of melding the effects of individual fibers by producing several reflected beams diverging from each other. Since only reflection is occurring rather than scattering, the angular spread 54 and therefore the numerical aperture of the fibers is retained at output end 56 of the mixing slab. Gaps in light due to broken fibers or poor packing are thus averaged out. Ideally, mixers will provide uniform illuminance or irradiance on their output surface even though the input is structured.

The mixing slab is more than five times longer (in z-dimension) than wide (in x-dimension), preferably in approximately an 8:1 ratio, though the exact ratio depends on the angle of light entering into the slab. Losses through the mixing slab can be minimized with appropriate choice of material and by keeping the length no longer than that necessary to provide the mixing. Some likely materials for the mixing slab include: fused silica, quartz, acrylic, or glass, but it may be comprised of any material transparent at the wavelengths being used, which has an index of refraction greater than that of air. The overall effect of the mixing slab is to retain high transmission, but average over the gaps in light profile caused by fiber bundle fabrication anomalies of size roughly comparable to or smaller than the fiber diameter.

Diffusing medium 34 (hereinafter also known as "diffuser") that follows the mixing slab in the light path is used to average out variations in angle but also to further reduce nonuniformities in brightness, particularly in the y-direction which is not homogenized by the mixing slab due to its large dimension. Diffusing transmission media typically are comprised of a transparent solid that either has suspended within it evenly distributed scattering centers 35 or has a coating of evenly distributed scattering centers on a surface. Diffuser 34 may also be comprised of holographic material which is composed of micro-refractive structures that have the effect of scattering and yet provide good transmissibility. It is critical that the evenly distributed scattering centers must be smaller in size than the resolution of interest, and that the scatter center-to-center distances be less than the resolution of interest. An ideal diffusing transmission medium can scatter an incoming light ray into an isotropic spherical distribution, however at a high cost in output intensity. Lower diffusivity media scatter incoming light at a particular angle into Gaussian angular distributions of varying spread, depending on the medium used. For the purposes of defect inspection, the degree of diffusivity vs. output intensity must be optimized for the particular application. Possible diffusing media include but are not restricted to: opal glass, textured plastic such as acrylic, and holographically patterned films such as those supplied by Physical Optics Co.

The lens system which may optionally follow the diffuser in the light path serves to re-collect the diffused light and to focus it into a high intensity beam of the desired shape and angular spread, therefore controlling the numerical aperture and angle of incidence of the illumination incident on the specimen. This lens is particularly important in dark-field applications.

Figure 6:
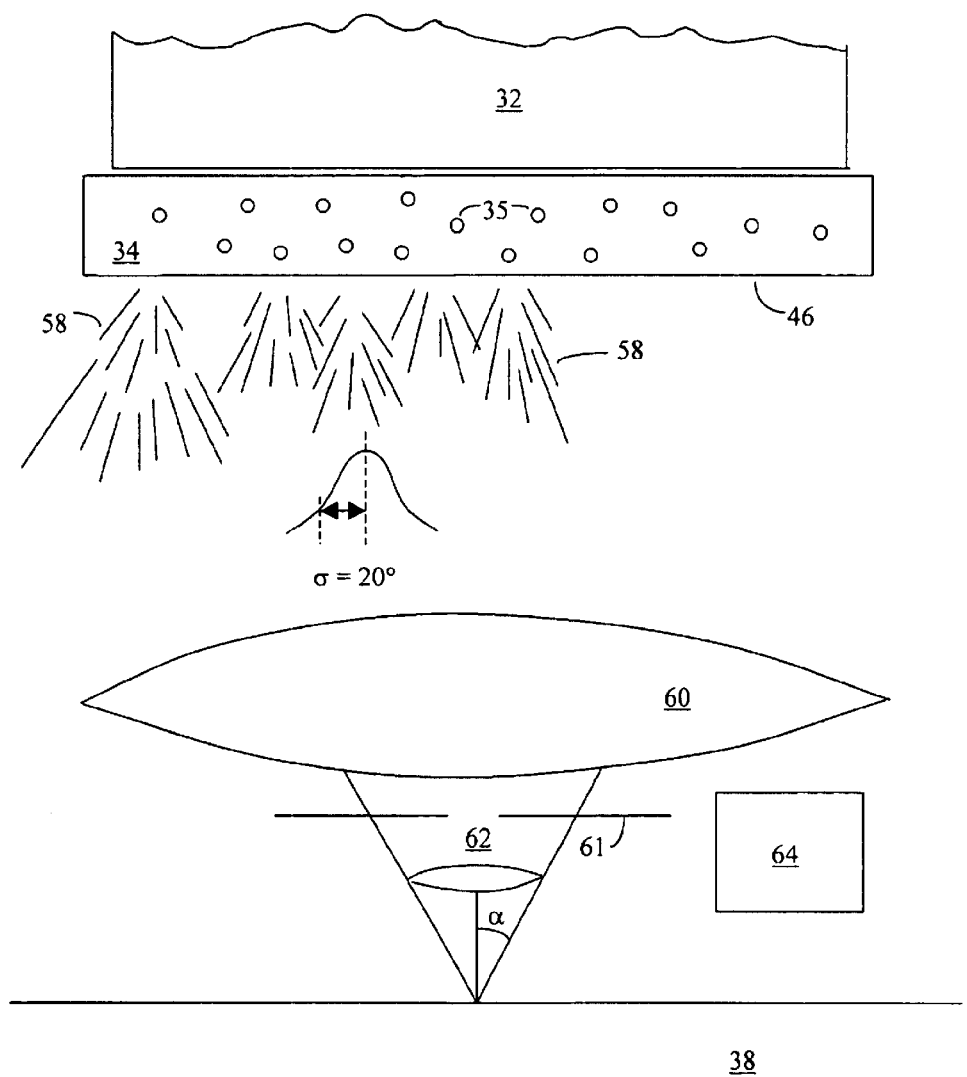
FIG. 6 illustrates an embodiment of the diffuser and lens portion of the inventive structure.

FIG. 6 illustrates an embodiment of the diffuser and lens portion of the inventive structure. For purposes of illustration, a single lens is shown. The output light 58 from diffuser 34 has a Gaussian profile in angle with half-angle θ having a one sigma distribution of 20 degrees. The lens 60, due to its proximity to the diffuser output end 46 (5–25 mm apart), collects a large percentage, 40–50%, of the diffused light and focuses it onto the sample 38 in an incident cone 62 having angular width α approximately 15 degrees. The incident light onto the sample therefore has a well defined numerical aperture. Optional aperture stop 61 having a slit therethrough (described hereinafter) may be positioned between the output of diffuser 34 and sample 38. Collection optics 64 may be positioned as shown or at other angles.

The inventive method is applied in the KLA-Tencor 2430 defect inspection system, which inspects wafers of diameter up to 300 mm. For this system, the output of a 200 W metal halide lamp (an approximate point source with diameter of about 1.5 mm) is directed into a fiber optic bundle with diameter of about 1 inch. The bundle is fanned into a fiber optic array 0.5 mm wide by 356 mm long. Fiber diameters are approximately 50 microns, and fibers are about seven feet in length. A mixing slab made of glass having dimensions x=2 mm by z=12.5 mm by y=356 mm is placed abutting the output of the fiber fan. A diffuser made of holographic film having 92% transmittance is placed about 3 mm from the output of the mixing slab. An anamorphic cylindrical lens system comprising two rods made of Poly Methyl Methacrylate (PMMA)—commonly known as acrylic and sold under the trade name of Lucite—placed about one cm from the diffuser output, then refocuses the linearly shaped beam into a beam incident on the sample which has dimensions 2.5 mm by 356 mm contained within an angle of approximately 27 degrees, and intensity of approximately 1.5 mW/mm$^2$. This compares with the Viper 2401 system which uses a fluorescent lamp tube that delivers an incident intensity on the sample of approximately 0.1 mW/mm$^2$. Total losses along the entire delivery system are approximately 45% fiber, 10% slab, 50% diffuser, 19% lenses. In order to satisfy the throughput requirements for the 2430 machine, the minimum value for the incident intensity on the sample is approximately 0.5 mW/mm$^2$. The inventive illumination delivery system provides ample illumination intensity.

Figure 7:
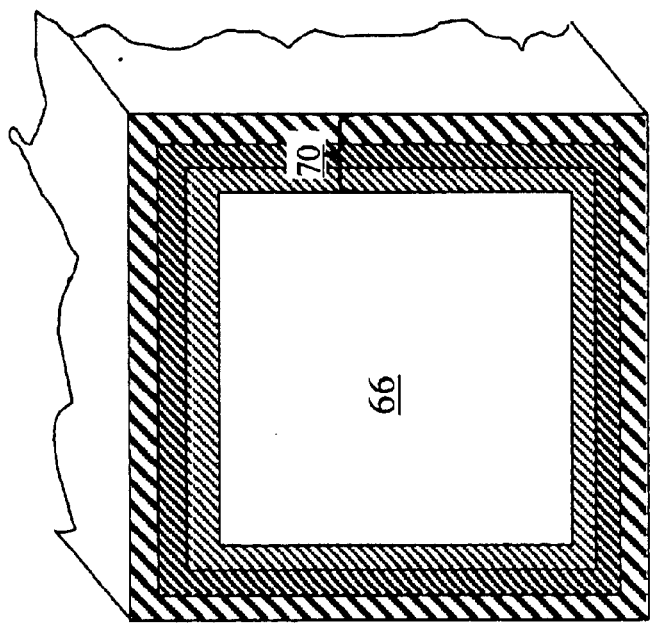
FIG. 7 illustrates a cross section of square cross section fibers clad in lower index material or GRIN material.
Figure 7:
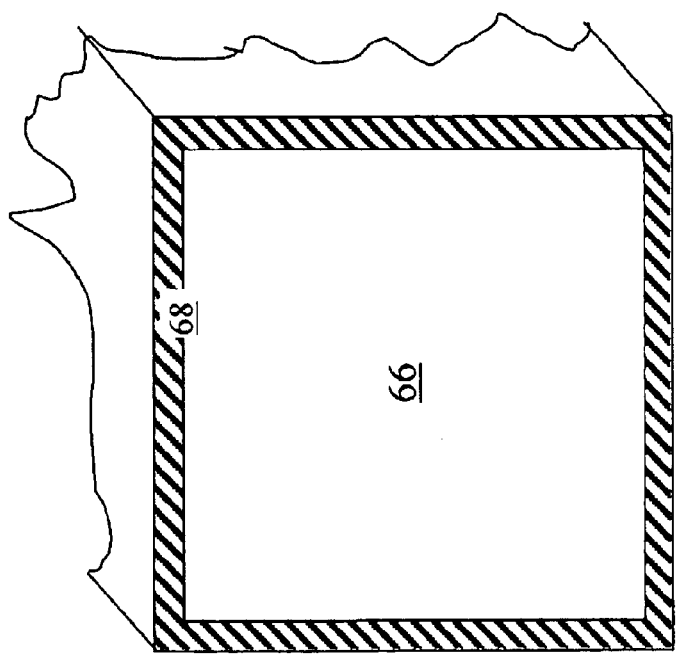

In an alternative embodiment, instead of homogenizer 32 being a mixing slab, it is a short array of optical fibers having square cross section. This short array would function as an array of homogenizing rods and would homogenize in both the x- and y-directions. Excellent aspect ratios can be achieved with fibers, which would in turn improve the homogeneity of the transmitted light. As shown in FIG. 7, Each fiber 66 would to be clad in lower refractive index material 68, or a GRIN (Gradient Index) approach with a GRIN region 70 could be used. The GRIN approach is described in U.S. Pat. Nos. 5,543,830; 6,252,722; 5,978,146; 5,959,783; and 5,638,479, all of which are hereby incorporated by reference. The short fiber array would need to be precisely and accurately assembled to avoid gaps and non-parallel fibers, so would need to be assembled in a manner similar to that used for GRIN lens arrays (as described in the above-cited patents), or by controlled winding of fiber followed by fiber fusing or encapsulation. The controlled winding method is used, for example, by the Schott Glass Co. of Mainz, Germany, for making coherent fiber bundles for endoscopy. The use of such a short square fiber array in place of the mixing slab would increase the mixing in the direction parallel to the illumination line, but would substantially increase the part cost.

Another alternative embodiment utilizes holographically generated diffusive materials which diffuse light differentially in x and y. Thus, by choosing the appropriate diffuser it is possible to trade off light intensity versus uniformity separately in the longitudinal and transverse directions.

A third alternative embodiment incorporates slits or apertures in opaque materials inserted into the illumination path, with the purpose of controlling the effective NA of the illumination. These apertures are functionally similar to aperture stops employed in Kohler illumination systems for microscopes. By limiting the NA of the illumination, the contrast on the image may be improved, although significant intensity loss will result.

The inventive approach is adaptable to varying fiber optic assembly types, shapes, and sizes. For example, fiber optic arrays may be made by epoxying fibers into the desired shape by heat treating to fuse fibers together. Fibers may be circular or square in profile. Use of square fibers provides the advantage of tighter packing density, but may have undesirable optical effects due to corners. Fiber sizes may vary, and the inventive approach may be more effective in the cases in which fabrication flaws are equal or less in magnitude to fiber size.

Our invention provides a line illumination source which is uniform at all positions across its length, and at all angles within its NA. It also provides the ability to have a uniform local NA. These qualities of the illumination source increase the detection sensitivity to diffractive structure variations from the sample. When used in conjunction with a fixed angle of collection optics, whether or not the collection angle is normal to the sample surface, the imaging is effectively telecentric. Both reflective (wherein the imaging optics are mirrors) and refractive (wherein the imaging optics are lenses) telecentricity can be achieved. In a well calibrated system this leaves the wafer or other sample under test as the only contributor to variations in the resultant image. This implementation yields the highest intrinsic signal to noise ratio from both illumination and collection contributions.

In a further potential application of the invention, fiber delivery is used when collection optics 64 comprise CIS or GRIN collection optics. A description of CIS collection optics as used in defect inspection is found in the commonly owned U.S. patent application Ser. No. 09/965,480 entitled "Systems and Methods for Inspection of Specimen Surfaces" by Eliezer Rosengaus and Lydia Young, filed on Sep. 24, 2001, which is hereby incorporated by reference.

It will be obvious to those skilled in the art that modifications may be made to the embodiments described herein without departing from the inventive concept. The order of components may be changed—the diffuser may be placed after the lens, or within a two part lens system. Diffusers of other transmittances can be used. Higher transmittances may result in less mixing than desired, but provide higher brightness. Lower transmittances may provide the desired uniformity, but reduce brightness more than desired. The properties for a diffuser may be selected according to the desired geometry of the resulting light beam, i.e., point, line, or area. For example, diffusion along the line would be an important factor for line geometry, while for an area geometry the selected diffusive material would need to provide the appropriate effect over the full area. The scope of the invention should be construed according to the claims.

We claim:

1. An illumination delivery apparatus comprising:
   a fiber optic bundle comprised of sufficiently high-transmittance material to incur intensity losses no greater than on the order of 45%, said fiber optic bundle having an input end for receiving input light from a light source and further having an output end, said fiber optic bundle input end having an input cross-sectional profile and said fiber optic bundle output end having an output cross-sectional profile, said input and output cross-sectional profiles having any shape;
   a homogenizer, said homogenizer providing multiple total internal reflections of light transmitted therethrough, said homogenizer having an input end and an output end, said homogenizer input end being proximal said output end of said fiber optic bundle, said homogenizer being of sufficiently high transmittance to incur intensity losses no greater than on the order of 10%;
   said homogenizer having an input cross-sectional profile similar in shape and size to said output cross-sectional profile of said fiber optic bundle output end;
   a diffusing medium proximal said output end of said homogenizer, said diffusing medium having an input end and an output end;
   said fiber optic bundle, homogenizer, and diffusing medium being configured such that a portion of any input light entering said input end of said fiber optic bundle and transmitted therethrough, is additionally transmitted through said homogenizer and said diffusing medium to yield a first shaped beam output, said first shaped beam output having substantial spatial uniformity, said first shaped beam output having an intensity, said intensity being sufficient to illuminate a sample surface, said first shaped beam output having an illumination numerical aperture.

2. The illumination delivery apparatus of claim 1, further including a light source for providing said input light, said light source positioned proximal said input end of said fiber optic bundle.

3. The illumination delivery apparatus of claim 1, further including:
   focusing optics comprised of sufficiently high-transmittance material to incur intensity losses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

4. The illumination delivery apparatus of claim 3, wherein said focusing optics are positioned between said output end of said diffuser and said sample surface.

5. The illumination delivery apparatus of claim 4, wherein said focusing optics comprise at least one lens.

6. The illumination delivery apparatus of claim 5, wherein said focusing optics comprise two lenses.

7. The illumination delivery apparatus of claim 6, wherein said lenses comprise an anamorphic cylindrical lens system.

8. The illumination delivery apparatus of claim 7, wherein said anamorphic cylindrical lens system comprises two acrylic rods.

9. The illumination delivery apparatus of claim 3, further including a light source for providing said input light, said light source positioned proximal said input end of said fiber optic bundle.

10. The illumination delivery apparatus of claim 1, wherein said shaped beam output has a linear dimension greater than 100 millimeters.

11. The illumination delivery apparatus of claim 10, wherein said shaped beam output is rectangular.

12. The illumination delivery apparatus of claim 11, where said rectangular beam output has an aspect ratio of approximately 700:1.

13. The illumination delivery apparatus of claim 11, further including:
   focusing optics comprised of sufficiently high-transmittance material to incur intensity losses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

14. The illumination delivery apparatus of claim 11, further including a light source for providing said input light, said light source positioned proximal said input end of said fiber optic bundle.

15. The illumination delivery apparatus of claim 1, wherein said homogenizer comprises a mixing slab having an input end and an output end and further having a length z, a width x, and a depth y, said length being the distance between said mixing slab input end and said mixing slab output end, said mixing slab being comprised of a material transparent to said input light and having an index of refraction greater than the index of refraction of air.

16. The illumination delivery apparatus of claim 15, wherein the ratio of said length to said width is greater than 5.

17. The illumination delivery apparatus of claim 16, wherein said ratio of said length to said width is approximately 8.

18. The illumination delivery apparatus of claim 15, wherein said mixing slab is comprised of a material selected from the group consisting of
fused silica, quartz, acrylic, and glass.

19. The illumination delivery apparatus of claim 15, further including:
focusing optics comprised of sufficiently high-transmittance material to incur intensity tosses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

20. The illumination delivery apparatus of claim 19, wherein:
said input end of said homogenizer is in the range between 0 and 3 mm from said output end of said fiber optic bundle;
said input end of said diffusing medium is in the range between 0 and 3 mm from said output end of said homogenizer; and
said input end of said focusing optics is in the range between 5 and 25 mm from said output end of said diffusing medium.

21. The illumination delivery apparatus of claim 15, further including a light source for providing said input light, said light source positioned proximal said input end of said fiber optic bundle.

22. The illumination delivery apparatus of claim 1, wherein said homogenizer comprises an array of optical fibers, each said optical fiber having a square cross section, said array being substantially free of gaps and non-parallel optical fibers.

23. The illumination delivery apparatus of claim 22, where each said optical fiber is clad in a material having a lower refractive index than the refractive index of said optical fiber.

24. The illumination delivery apparatus of claim 22, where each said optical fiber has a GRIN (Gradient Index) region.

25. The illumination delivery apparatus of claim 22, further including:
focusing optics comprised of sufficiently high-transmittance material to incur intensity losses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

26. The illumination delivery apparatus of claim 22, further including a light source for providing said input light, said light source positioned proximal said input end of said fiber optic bundle.

27. The illumination delivery system of claim 1, wherein said diffusing medium comprises a transparent solid having a surface and an interior region, said diffusing medium including evenly distributed scattering centers, said evenly distributed scattering centers being either suspended in said interior region of said transparent solid or being coated on said surface of said transparent solid.

28. The illumination delivery system of claim 27, wherein said diffusing medium is comprised of opal glass or textured plastic.

29. The illumination delivery system of claim 1, wherein said diffusing medium comprises a holographic diffuser including micro-refractive structures.

30. The illumination delivery system of claim 1, further including CIS collection optics.

31. The illumination delivery system of claim 1, further including:
at least one aperture stop comprising an opaque material having a slit therethrough, said at least one aperture stop being positioned between said output end of said diffuser and a sample surface;
said at least one aperture stop limiting said illumination numerical aperture onto said sample surface.

32. A macro inspection system for inspecting a sample surface, said inspection system requiring illumination having high spatial and angular uniformity over a linear dimension greater than 100 millimeters;
said macro inspection system including the illumination delivery apparatus of claim 1.

33. The macro inspection system of claim 32, further including a light source for providing said input light, said light source positioned proximal said input end of said fiber optic bundle.

34. The macro inspection system of claim 32, further including:
focusing optics comprised of sufficiently high-transmittance material to incur intensity losses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

35. The macro inspection system of claim 34 wherein a sample surface is the surface of a wafer.

36. The macro inspection system of claim 35 wherein said wafer has a diameter greater than or equal to 200 mm.

37. The macro inspection system of claim 36 wherein said shaped beam output is scanned across said wafer surface in one direction only.

38. The macro inspection system of claim 36 wherein said intensity of said shaped beam output is at least 0.5 mW/mm$^2$.

39. The macro inspection system of claim 34 further including a light source for providing said input light, said light source positioned proximal said input end of said fiber optic bundle.

40. The macro inspection system of claim 39 wherein said light source comprises a 200 W metal halide lamp, said lamp being an approximate point source with diameter of approximately 1.5 mm.

41. The macro inspection system of claim 32 wherein said shaped beam output has an angular spread not more than 27 degrees.

42. The macro inspection system of claim 32 wherein:

said fiber optic bundle has a diameter of approximately 1 inch;

said output cross sectional profile of said fiber optic bundle is rectangular and has a width of approximately 0.5 mm and a length of approximately 356 mm;

said homogenizer is a glass mixing slab having width x of approximately 2 mm, length z of approximately 12.5 mm, and depth y of approximately 356 mm, said input end of said homogenizer abutting said output of said fiber optic bundle;

said diffusing medium is a holographic diffuser comprised of holographic film having approximately 92% transmittance, said diffuser being positioned approximately 3 mm from said output end of said homogenizer;

said inspection system further including focusing optics, said focusing optics being an anamorphic cylindrical lens system comprising two acrylic rods, said lens system being positioned approximately one cm from said output end of said diffuser;

said shaped beam output having dimensions approximately 2.5 mm by 356 mm, having intensity of approximately 1.5 mW/mm$^2$, and having an angular spread of approximately 27 degrees.

43. A method of illuminating a sample surface comprising the steps of:

providing a light source to produce input light;

providing a fiber optic bundle comprised of sufficiently high-transmittance material to incur intensity losses no greater than on the order of 45%, said fiber optic bundle having an input end for receiving input light from a light source and further having an output end, said fiber optic bundle input end having an input cross-sectional profile and said fiber optic bundle output end having an output cross-sectional profile, said input and output cross-sectional profiles having any shape;

providing a homogenizer, said homogenizer providing multiple total internal reflections of light transmitted therethrough, said homogenizer having an input end and an output end, said homogenizer input end being proximal said output end of said fiber optic bundle, said homogenizer being of sufficiently high transmittance to incur intensity losses no greater than on the order of 10%;

said homogenizer having an input cross-sectional profile similar in shape and size to said output cross-sectional profile of said fiber optic bundle output end;

providing a diffusing medium proximal said output end of said homogenizer, said diffusing medium having an input end and an output end;

directing said input light onto said input end of said fiber optic bundle to cause a portion of said input light to be transmitted through said fiber optic bundle, said homogenizer, and said diffuser to yield a shaped beam output having substantial spatial uniformity and further having an intensity; and directing said shaped beam output onto said sample surface.

44. The method of claim 43 further including the steps of:

directing said shaped beam output through focusing optics to provide said shaped beam output with substantial angular uniformity prior to directing said shaped beam output onto said sample surface.

45. An illumination delivery apparatus comprising;

a homogenizer, said homogenizer providing multiple total internal reflections of light transmitted therethrough, said homogenizer having an input end and an output end, said homogenizer having the input end for receiving input light from a light source, said homogenizer being of sufficiently high transmittance to incur intensity losses no greater than on the order of 10%;

a diffusing medium proximal said output end of said homogenizer, said diffusing medium having an input end and an output end;

said homogenizer and diffusing medium being configured such that a portion of any input light entering said input end of said homogenizer and being transmitted therethrough, is additionally transmitted through said diffusing medium to yield a first shaped beam output, said first shaped beam output having substantial spatial uniformity, said first shaped beam output having an intensity, said intensity being sufficient to illuminate a sample surface, said first shaped beam output having an illumination numerical aperture.

46. The illumination delivery apparatus of claim 45, wherein said first shaped beam output has a linear dimension greater than 100 millimeters.

47. The illumination delivery apparatus of claim 45, further including a light source for providing said input light, said light source positioned proximal said input end of said homogenizer.

48. The illumination delivery apparatus of claim 45, further including:

focusing optics comprised of sufficiently high-transmittance material to incur intensity losses no greater than on the order of 19%, said focusing optics being positioned between said homogenizer and a sample surface, said focusing optics being configured such that a portion of light transmitted through said homogenizer is additionally transmitted through said focusing optics to yield a second shaped beam output, said second shaped beam output having substantial angular uniformity.

49. The illumination delivery apparatus of claim 48, wherein said shaped beam output has a linear dimension greater than 100 millimeters.

50. The illumination delivery apparatus of claim 48, further including a light source for providing said input light, said light source positioned proximal said input end of said homogenizer.

51. The illumination delivery apparatus of claim 48, wherein said focusing optics are positioned between said output end of said diffusing medium and said sample surface.

52. A macro inspection system for inspecting a sample surface, said inspection system requiring illumination having high spatial and angular uniformity over a linear dimension greater than 100 millimeters;

said macro inspection system including the illumination delivery apparatus of claim 46.

53. The macro inspection system of claim 52 wherein said sample surface is the surface of a wafer.

54. The macro inspection system of claim 53 wherein said wafer has a diameter greater than or equal to 200 mm.

55. The macro inspection system of claim 53 wherein said shaped beam output is scanned across said wafer surface in one direction only.

56. The macro inspection system of claim 53 wherein said intensity of said shaped beam output is at least 0.5 mW/mm$^2$.

57. The macro inspection system of claim 52 further including a light source for providing said input light, said light source positioned of proximal said input end of said homogenizer.

58. A method of illuminating a sample surface comprising the steps of:

providing a light source to produce input light;

providing a homogenizer, said homogenizer providing multiple total internal reflections of light transmitted therethrough, said homogenizer having an input end for receiving input light from said light source and further having an output end, said homogenizer being of sufficiently high transmittance to incur intensity losses no greater than on the order of 10%;

providing a diffusing medium proximal said output end of said homogenizer, said diffusing medium having an input end and an output end;

directing said input light onto said input end of said homogenizer to cause a portion of said input light to be transmitted through said homogenizer and said diffuser to yield a shaped beam output having substantial spatial uniformity and further having an intensity; and directing said shaped beam output onto said sample surface.

59. The method of claim 58 further including the steps of:

directing said shaped beam output through focusing optics to provide said shaped beam output with substantial angular uniformity prior to directing said shaped beam output onto said sample surface.

* * * * *